(12) United States Patent
Jordan (10) Patent No.: US 10,449,071 B2
(45) Date of Patent: Oct. 22, 2019

(54) STENT DEPLOYMENT SYSTEM WITH INTEGRATED DIGITAL CAMERA AND DILATION BALLOON

(75) Inventor: Gary Jordan, Litchfield, NH (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1236 days.

(21) Appl. No.: 13/331,590

(22) Filed: Dec. 20, 2011

(65) Prior Publication Data

US 2012/0165916 A1 Jun. 28, 2012

Related U.S. Application Data (60) Provisional application No. 61/425,801, filed on Dec. 22, 2010.

(51) Int. Cl.
*A61F 2/95* (2013.01)
*A61F 2/966* (2013.01)

(52) U.S. Cl.
CPC .............. *A61F 2/95* (2013.01); *A61F 2/966* (2013.01); *A61F 2250/0091* (2013.01)

(58) Field of Classification Search
CPC .... A61F 2220/0091; A61F 2/95; A61F 2/966; A61F 2/962; A61F 2/958; A61F 2/954; A61F 2002/9583; A61F 2002/9586; A61F 2002/9505; A61F 2002/9511; A61F 2002/9517; A61F 2002/9522; A61F 2002/9528; A61F 2002/9534
USPC ................................................ 623/1.11, 1.12
See application file for complete search history.

(56) References Cited

U.S. PATENT DOCUMENTS

| 6,156,005 | A | * | 12/2000 | Theron | A61M 25/104 604/101.05 |
|---|---|---|---|---|---|
| 6,447,835 | B1 | | 9/2002 | Wang et al. | |
| 6,890,348 | B2 | | 5/2005 | Sydney et al. | |
| 6,953,431 | B2 | | 10/2005 | Barthel | |
| 8,177,831 | B2 | * | 5/2012 | Andreas | A61F 2/91 623/1.11 |
| 2002/0193863 | A1 | * | 12/2002 | Rourke | A61F 2/95 623/1.11 |
| 2003/0050686 | A1 | | 3/2003 | Raeder-Devens | |
| 2004/0015052 | A1 | | 1/2004 | Barthel | |
| 2004/0193243 | A1 | * | 9/2004 | Mangiardi | A61F 2/95 623/1.11 |
| 2006/0116750 | A1 | * | 6/2006 | Hebert | A61F 2/95 623/1.11 |
| 2006/0271154 | A1 | * | 11/2006 | Woodall | A61B 17/12136 623/1.11 |
| 2007/0233221 | A1 | | 10/2007 | Raju | |

(Continued)

FOREIGN PATENT DOCUMENTS

DE 19547538 A1 6/1997
EP 0839504 A1 5/1998

*Primary Examiner* — Kathleen S Holwerda
*Assistant Examiner* — Sarah A Simpson
(74) *Attorney, Agent, or Firm* — Seager, Tufte & Wickhem, LLP (57) ABSTRACT

The deployment device includes at least one sheath, a dilation balloon, a transparent tip extending between the at least one sheath and the dilation balloon, a prosthesis, an inner tubular member and a camera to allow visualization of the stricture and prosthesis prior, during, and after deployment without the use of an endoscope. The sheath includes a camera extending from one end.

20 Claims, 4 Drawing Sheets

(56) References Cited

U.S. PATENT DOCUMENTS

| | | | |
|---|---|---|---|
| 2008/0125850 A1* | 5/2008 | Andreas | A61F 2/91 623/1.12 |
| 2008/0228258 A1* | 9/2008 | Gerdts et al. | 623/1.11 |
| 2009/0299135 A1* | 12/2009 | Spivey | A61B 1/00073 600/106 |
| 2010/0168612 A1 | 7/2010 | Ducharme | |
| 2012/0041533 A1* | 2/2012 | Bertolino | A61B 1/00181 623/1.11 |
| 2012/0041534 A1* | 2/2012 | Clerc et al. | 623/1.11 |
| 2012/0232342 A1* | 9/2012 | Reydel | A61B 1/00082 600/104 |

\* cited by examiner

STENT DEPLOYMENT SYSTEM WITH INTEGRATED DIGITAL CAMERA AND DILATION BALLOON

CROSS-REFERENCE TO RELATED APPLICATIONS

This application claims priority to provisional application Ser. No. 61/425,801, filed Dec. 22, 2010, the contents of which are hereby incorporated by reference.

FIELD OF THE INVENTION

Embodiments are directed to medical devices, and in particular to a stent deployment system adapted for advancing a camera to allow visualization of stent deployment.

BACKGROUND OF THE INVENTION

Stents and stent delivery assemblies are utilized in a number of medical procedures and situations, and as such their structure and function are well known. A stent is a generally cylindrical prosthesis that is introduced via a catheter into a lumen of a body cavity or vessel. The stent is introduced into the cavity or vessel with a generally reduced diameter and then is expanded to the diameter of the cavity or vessel. In its expanded configuration, the stent supports and reinforces the cavity/vessel walls while maintaining the cavity/vessel in an open, unobstructed condition.

Typically, when deploying an endoscopically delivered stent in a body cavity of interest, a guidewire is introduced into the body cavity through a working lumen defined in an endoscope to ensure proper placement of the prosthesis. The guidewire is used to ensure that the device is properly positioned and the deployment device is maintained in the proper position during deployment of the prosthesis. A physician advances an endoscope to identify the stricture location by observing an image received from the distal end of the endoscope. A dilation device is advanced through the scope and the dilation device is used to dilate the stricture. Once the position of interest, as observed by the endoscope, is identified, internal and/or external markers are placed to identify and indicate the stricture location. The endoscope and the dilation device are then withdrawn. Thereafter, a stent delivery catheter is advanced to the stricture location, using fluoroscopy (x-ray imaging of a moving object), and the deploy stent. To observe and ensure proper deployment of the stent, the endoscope is re-introduced to confirm stent placement. In addition, fluoroscopy is often used to ensure proper placement and deployment of the stent, as well known in the art.

The use of an endoscope in combination with a dilation device, however, requires additional steps to locate the stricture, introduce a dilation device, and placing markers. Still further, use of fluoroscopy to confirm proper positioning of a stent is a relatively cumbersome procedure and requires additional safety mechanisms for the patients as well as the doctors and their assistants.

A need exists for a vision system that is integral with the stent delivery and dilation system to provide a device that deploys, dilates and provides imaging in a single device. A need exists for a single device that provides visualization, dilation and deployment of a prosthesis without the required use of fluoroscopy and/or a separate endoscope.

SUMMARY OF THE INVENTION

A prosthesis deployment system including at least one sheath removably covering a prosthesis therein. The at least one sheath includes a distal end, a proximal end, an outer surface and a channel extending between the distal end and the proximal end, the channel defining an inner wall. The prosthesis extends in a compressed state within the longitudinal channel. A dilation balloon extends adjacent to the at least one sheath. A transparent tip extends between the distal end of the at least one sheath and the dilation balloon. An inner tubular member extends through the prosthesis, the transparent tip and the dilation balloon. A camera may be provided to the distal end of the at least one sheath. Camera can be a chip or an optical fiber that can be attached to the distal end.

Further, some embodiments of a stent deployment system include an inner sheath removably covering a stent therein. The inner sheath includes a distal end, a proximal aid, an outer surface and a channel extending between the distal end and the proximal end, the channel defining an inner wall. The stent extends in a compressed state within the longitudinal channel. An outer sheath extends about the exterior of the inner sheath. The outer sheath is independently movable from the inner sheath, and the outer sheath includes an outer distal end. A camera can be attached to the outer distal end of the outer sheath. A dilation balloon is adjacent the inner sheath. A transparent tip may extend between the inner sheath and the dilation balloon. The transparent sheath abuts the distal end. An inner tubular member is slidably extendable through the stent, the transparent tip and the dilation balloon. The inner tubular member is attached to the dilation balloon and transparent tip. The inner tubular member includes an elongated inner shaft with a distal tip at one end.

Additionally, one embodiment provides a method for intraluminally positioning a prosthesis including the steps of providing a deployment system, activating the camera to provide images during positioning of the prosthesis, positioning the deployment system within a body lumen, advancing the dilation balloon through a stricture within the body lumen, expanding the dilation balloon within the stricture, and slidably retracting the at least one sheath relative to the inner tubular member to uncover the prosthesis and allow the prosthesis to radially expand against a wall of bodily lumen. The step of providing a deployment system includes a deployment system including at least one sheath removably covering a prosthesis therein, the at least one sheath includes a distal end, a proximal end, an outer surface and a longitudinal channel extending between the distal end and the proximal end, the channel defining an inner wall, the prosthesis extending in a compressed state within the longitudinal channel, a dilation balloon adjacent the at least one sheath, a transparent tip extending between the at least one sheath and the dilation balloon, an inner tubular member slidably extending through the prosthesis, the inner tubular member includes an elongated inner shaft with a distal tip at one end, and a camera can be attached to the distal end of the at least one sheath.

These and other features of the invention will be more fully understood from the following description of specific embodiments of the invention taken together with the accompanying drawings.

BRIEF DESCRIPTION OF THE DRAWINGS

Corresponding reference characters indicate corresponding parts throughout the several views of the drawings.

DETAILED DESCRIPTION OF THE INVENTION

The embodiments of a delivery device described herein incorporates four separate devices of distinct function into one delivery device 10, 30. In some embodiments, the delivery device includes a guide wire system to locate and measure stricture, a balloon catheter system to provide inflation/deflation of a balloon at a stricture in a lumen, an imaging system to view stricture and to locate placement of the stent and a stent deployment system to deploy a stent at stricture location. Currently, multiple devices are needed with multiple steps of introducing and removing various devices or systems, in order to complete a procedure of placing a stent at a stricture point in the lumen.

The embodiments described herein eliminate the complication of multiple devices, multiple introductions, and limited active viewing throughout the procedure. Each of the delivery device embodiments described herein is a single device requiring only a single entry into the lumen, a single removal of the device, and provides for continuous viewing throughout the procedure, unlike the currently available devices.

In at least one embodiment, the deployment device is used to deploy various implants or prostheses. One embodiment is a deployment device including a dilation balloon, at least one sheath removably covering a prosthesis, an inner tubular member extending through the lumen of the stent and the dilation balloon, a transparent tip, and the inner tubular member extending through and attached to at least one the stent and the dilation balloon and a transparent tip. The transparent tip extends between the at least one sheath and the dilation balloon, and at least one imaging device or imaging lumen for an imaging device may be integrally formed, attached to, or movable with respect to the at least one sheath. The imaging device may be flush or protrude from the end of the at least one sheath.

Figure 1:
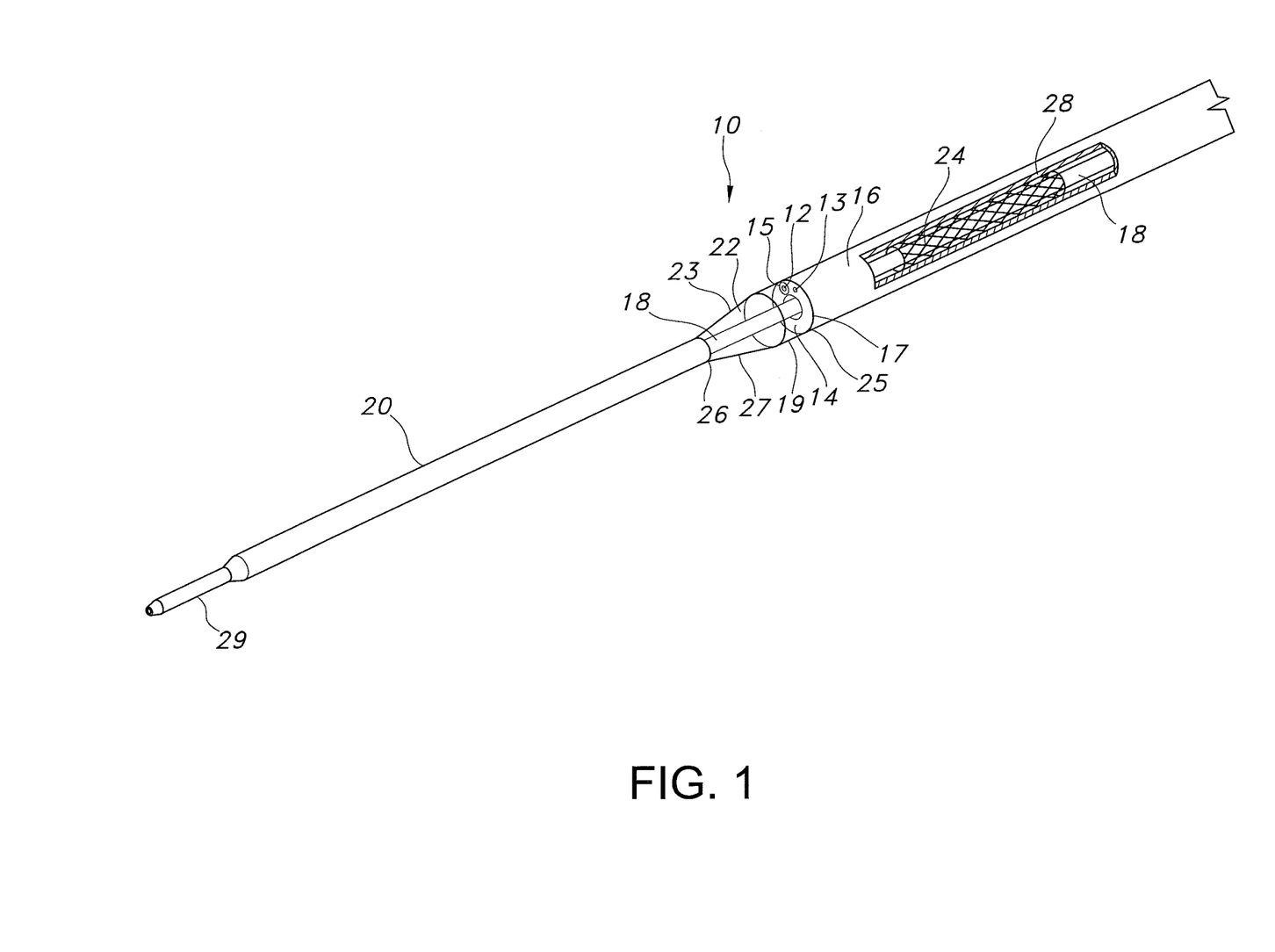
FIG. 1 is a schematic view of a delivery system that includes a sheath, a dilation balloon, a transparent tip with an imaging device internal therein.
Figure 1A:
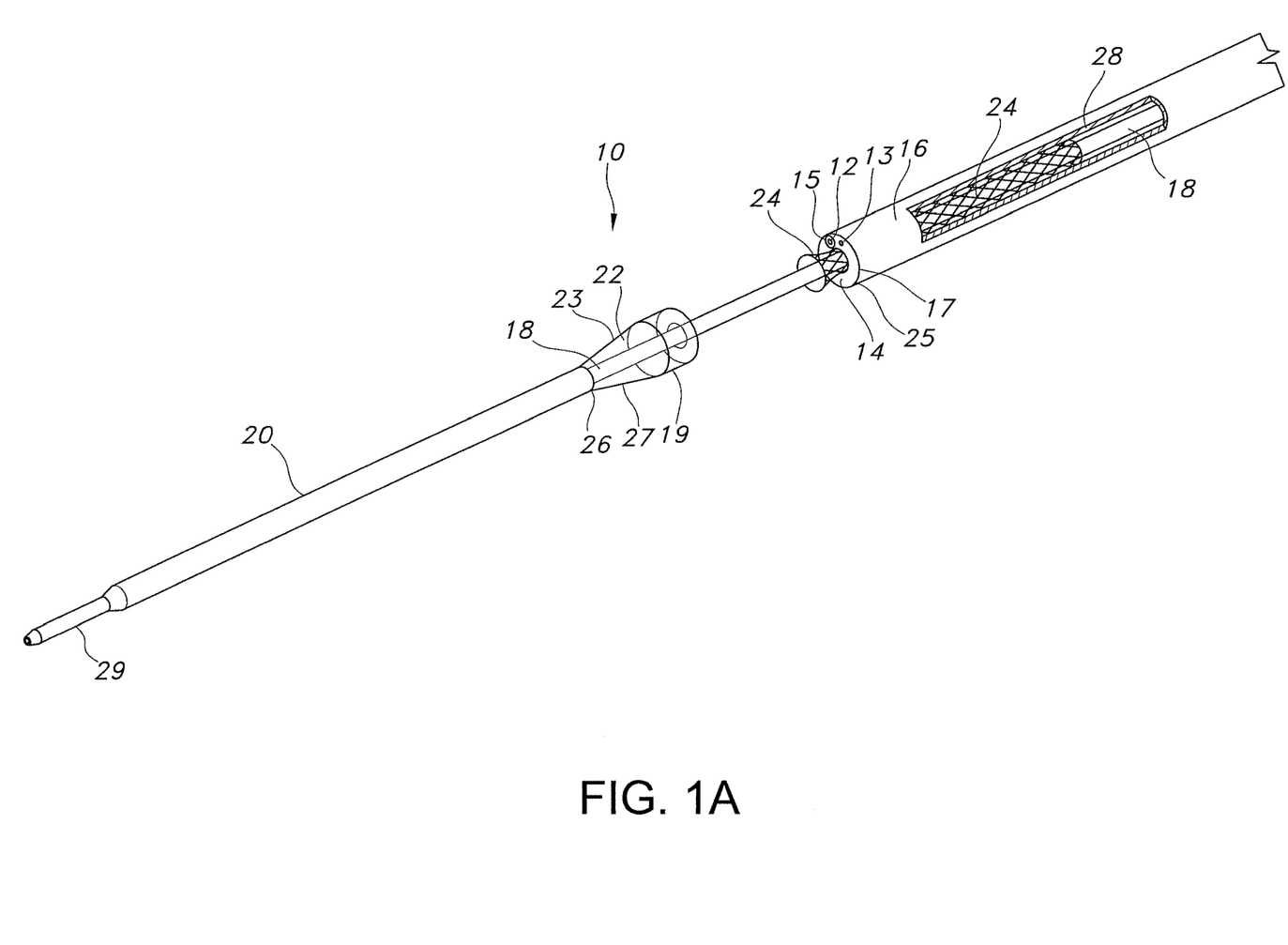
FIG. 1a is a schematic view of the delivery system of FIG. 1 showing the sheath being removed to release the stent therein.

Referring to the drawings and more specifically to FIGS. 1 and 1*a*, the deployment device 10 shown has a transparent tip 22 for visual access therethrough by an imaging device 12 located within a lumen 15 of sheath 16. The deployment device 10 may include a sheath 16 having an imaging device 12 thereon or therethrough, a dilation balloon 20, a transparent tip 22 and an inner member 18. The transparent tip 22 extends between the sheath 16 and dilation balloon 20, and an inner member 18 extends through the sheath 16. The inner member 18 extends through and is attached to the transparent tip 22 and the dilation balloon 20. The inner member 18 is a hollow tube with one or more lumens for directing inflation fluid to/from the balloon 20 for inflation/deflation of the dilation balloon 20. The dilation balloon 20 is attached at either end to the inner member 18. The imaging device 12 can extend through an imaging lumen 15 within the sheath 16. The end of the imaging device 12 can either be flush with the distal end 14 or protrude from the distal end 14 into a void in the transparent tip 22. The imaging device 12 allows for evaluation of the anatomy prior to stent release and observation of the proximal extremity of the stent 24 during stent release. After the stent 24 has been released, the imaging device 12 can be used to confirm stent placement and re-inspect the anatomy. Further, the sheath 16 can have an illumination device 13 to provide illumination within the lumen. The imaging device 12 and illumination device 13 may be located side-by-side or at different locations along the distal end 14 of the sheath 16. It is further contemplated that the sheath 16 and inner member 18 can rotate independently from each other to allow for visualization at different perspectives.

FIG. 1 shows transparent tip 22 having a proximal end 25, a distal end 26 and transparent material 27 extending therebetween. The transparent tip 22 is a solid transparent molded piece of material which is attached to the inner member 18. The distal end 26 has a smaller diameter than the proximal end 25. The distal end 26 abuts the dilation balloon 20. The proximal end 25 abuts the distal end 14 of the sheath 16. Extending from the proximal end 25 is a solid cylindrical band portion 19 having a circumference that is similar to the circumference 17 of the distal end 26. The solid distal portion 23 of the transparent tip 22 has a conical shape which is continuously formed and expands from the smaller diameter of the distal end 26 to the diameter of the cylindrical band of the proximal end 25. The transparent tip 22 surrounds the distal end 14 of the sheath 16 and may abut or enclose the imaging device 12 depending if the imaging device 12 protrudes into the cylindrical band portion 19. The transparent tip 22 may be solid with a space(s) carved out therein for the camera or optical fiber, imaging device 12, and/or for an illumination device 13.

FIG. 1*a* shows the deployment device 10 with the sheath 16 being removed to deploy the stent 24 therein. The transparent tip 22 is attached to the inner member 18 such that as the sheath 16 is slidably moved along the inner member 18, the transparent tip 22 remains in place.

FIGS. 1 and 1*a* show a cutaway portion of the sheath 16 to show stent 24 retained within the sheath 16 in a compressed state. Upon removal of the sheath 16 the stent 24 is permitted to expand into the lumen.

Figure 2:
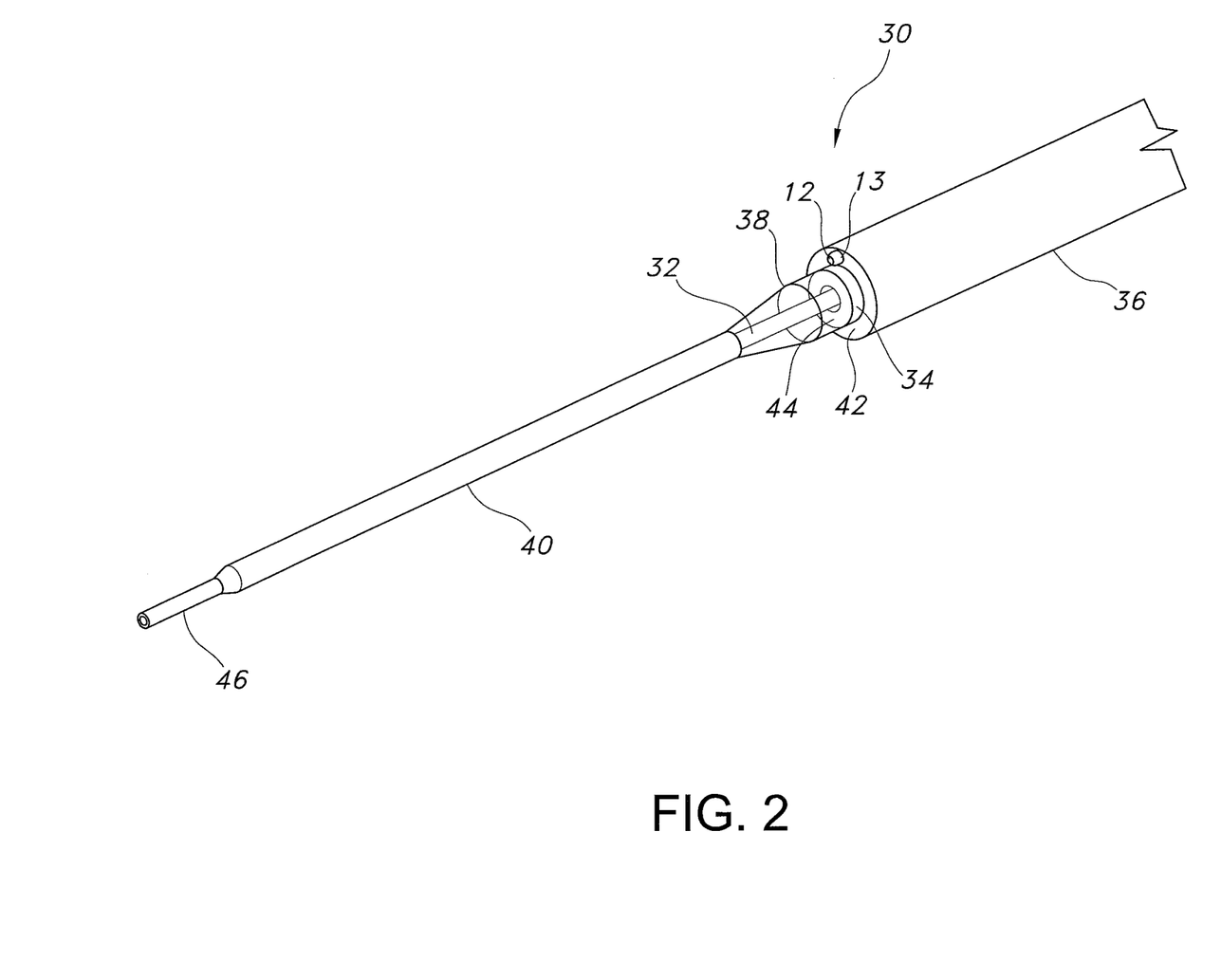
FIG. 2 is a schematic view of a delivery system that includes an outer sheath with an imaging device, an inner sheath with a transparent tip and a dilation balloon.
Figure 3:
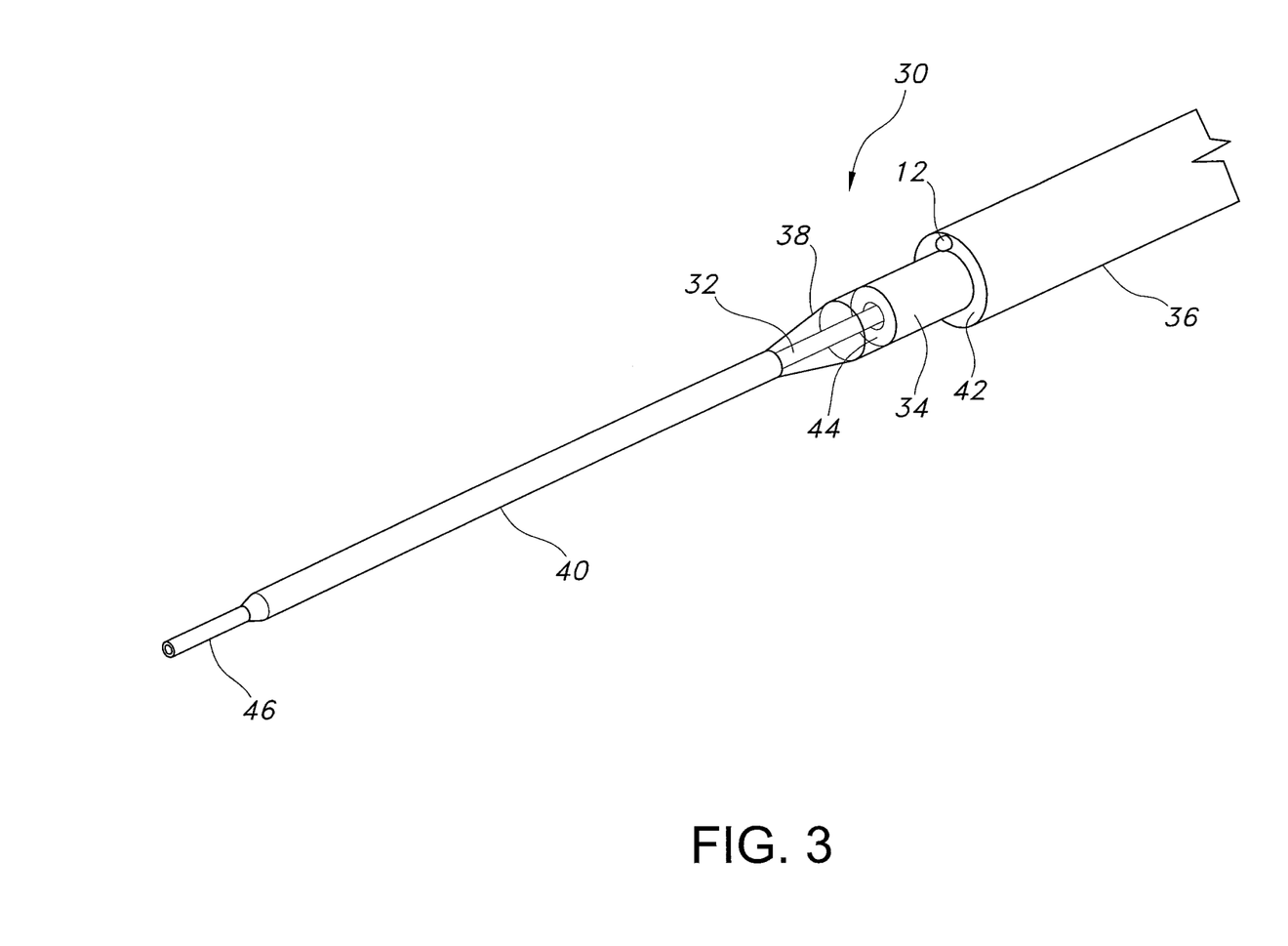
FIG. 3 is a schematic view of the delivery system of FIG. 2 with the outer sheath partially withdrawn.

FIGS. 2-3 show a deployment device 30 which is similar to deployment device 10 of FIGS. 1 and 1*a*. The devices of FIGS. 2-3 may include the inner sheath, transparent tip, dilation balloon and an imaging device as previously described with regards to FIGS. 1 and 1*a*. The devices of FIGS. 2-3 further include an additional sheath, i.e., outer sheath 36. An imaging device 12 is integrally formed on the outer sheath 36 external to the transparent tip 38. FIG. 2 shows deployment device 30 including an inner member 32, a middle sheath 34, an outer sheath 36, a transparent tip 38, and a dilation balloon 40. The outer sheath 36 and/or the middle sheath 34 may include an imaging device 12 locatable on distal end 42 or 44, respectively. It is contemplated that the imaging device 12 can be located in a variety of positions along the distal end. Further, the imaging device 12 can be a rotation camera such that it moves/rotates to different positions/angles within its socket. Additionally, the individual sheaths 34, 36 and inner member 32 can rotate independently from each other to allow for better visualization. The imaging device 12 allows for evaluation of the anatomy prior to stent release and allows for observation of the proximal extremity of the stent during stent release. After the stent 24 has been released, the imaging device 12 can be used to confirm stent placement and re-inspect the anatomy. The sheath(s) may also include an illumination device 13 to provide illumination within the lumen. The imaging device 12 and illumination device 13 may be located side-by-side or at different locations along the circumference of either or both sheaths 34, 36.

The middle sheath 34 contains the stent (not shown) in a compressed state. The outer sheath 36 may be rotated about the middle sheath 34 to provide various angles of viewing. The outer sheath 36 may be withdrawn or the middle sheath 34 may be advanced outwardly from the outer sheath 36 to expose the middle sheath 34 as shown in FIG. 3. The middle sheath 34 is then retracted to expose the stent within and allow for radial expansion thereof.

The transparent tip 22, 38 is formed from polymers, elastomers, silica and other materials known in the art which provide transparency. The transparent tip 22, 38 may be formed by blow molding.

The sheaths 16, 34, 36 and inner tubular members 18, 32 may be formed of a body compatible material. Desirably, the biocompatible material may be a biocompatible polymer. Examples of suitable biocompatible polymers may include, but are not limited to, polyolefins such as polyethylene (PE), high density polyethylene (HDPE) and polypropylene (PP), polyolefin copolymers and terpolymers, polytetrafluoroethylene (PTFE), polyethylene terephthalate (PET), polyesters, polyamides, polyurethanes, polyurethaneureas, polypropylene and, polycarbonates, polyvinyl acetate, thermoplastic elastomers including polyether-polyester block copolymers and poly amide/polyether/polyesters elastomers, polyvinyl chloride, polystyrene, polyacrylate, polymethacrylate, polyacrylonitrile, polyacrylamide, silicone resins, combinations and copolymers thereof, and the like. Desirably, the biocompatible polymers include polypropylene (PP), polytetrafluoroethylene (PTFE), polyethylene terephthalate (PET), high density polyethylene (HDPE), combinations and copolymers thereof, and the like. The biocompatible material may be a biocompatible metals including, but not limited to, nitinol, stainless steel, silver, and other materials as known in the art. Materials for the sheaths 16, 34, 36 and/or inner members 18, 32 may be the same or different.

The sheaths 16, 34, 36 and/or inner members 18, 32 may also have a surface treatment and/or coating on their inner surface, outer surface or portions thereof. A coating need not be applied to all of the sheaths 16, 34, 36 and/or inner members 18, 32 may be coated, uncoated, partially coated, and the like. Useful coating materials may include any suitable biocompatible coating. Non-limiting examples of suitable coatings include polytetrafluoroethylene, silicone, hydrophilic materials, hydrogels, and the like. Useful hydrophilic coating materials may include, but are not limited to, alkylene glycols, alkoxy polyalkylene glycols such as methoxypolyethylene oxide, polyoxyalkylene glycols such as polyethylene oxide, polyethylene oxide/polypropylene oxide copolymers, polyalkylene oxide-modified polydimethylsiloxanes, polyphosphazenes, poly(2-ethyl-2-oxazoline), homopolymers and copolymers of (meth)acrylic acid, poly(acrylic acid), copolymers of maleic anhydride including copolymers of methyl vinyl ether and maleic acid, pyrrolidones including poly(vinylpyrrolidone) homopolymers and copolymers of vinyl pyrrolidone, poly(vinylsulfonic acid), acryl amides including poly(N-alkylacrylamide), poly(vinyl alcohol), poly(ethyleneimine), polyamides, poly(carboxylic acids), methyl cellulose, carboxymethylcellulose, hydroxypropyl cellulose, polyvinylsulfonic acid, water soluble nylons, heparin, dextran, modified dextran, hydroxylated chitin, chondroitin sulphate, lecithin, hyaluranon, combinations and copolymers thereof, and the like. Non-limiting examples of suitable hydrogel coatings include polyethylene oxide and its copolymers, polyvinylpyrrolidone and its derivatives; hydroxyethylacrylates or hydroxyethyl(meth) acrylates; polyacrylic acids; polyacrylamides; polyethylene maleic anhydride, combinations and copolymers thereof, and the like. Additional details of suitable coating materials and methods of coating medical devices with the same may be found in U.S. Pat. Nos. 6,447,835 and 6,890,348, the contents of which are incorporated herein by reference. Such coatings and/or surface treatment may be desirably disposed on the inside or a portion thereof of the sheaths 16, 34, 36 to aid, if desired, in loading and/or deploying of the prosthesis 24. Further, sheaths 16, 34, 36 and/or inner members 18, 32 may also have see-through portions to aid the prosthesis delivery procedure. Such portions may be transparent, substantially transparent, translucent, substantially translucent and the like. Additional details of delivery devices having such transparent and or translucent portions may be found in U.S. Patent Application Publication No. 2003/0050686 A1 to Raeder-Devens et al., the contents of which are incorporated herein by reference. Further, the sheaths 16, 34, 36 and/or inner members 18, 32 may include reinforcement members including, but not limited to, braided fibers of polymer or metal, or variable stiffener sections.

While the stent 24 may be formed of metals, plastics or other materials, it is preferred that a biocompatible material or construction is employed. Useful biocompatible materials may include, but are not limited to biocompatible metals, biocompatible alloys, biocompatible polymeric materials, including biocompatible polymeric materials and bioabsorbable or biodegradable polymeric materials, materials made from or derived from natural sources, and combinations thereof. Useful biocompatible metals or alloys may include, but not limited to, nitinol, stainless steel, cobalt-based alloy such as Elgiloy, platinum, gold, titanium, tantalum, niobium, polymeric materials, and combinations thereof. Useful biocompatible polymeric materials include, but are not limited to, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, silks, and polytetrafluoroethylenes. The polymeric materials may further include a metallic, a glass, ceramic or carbon constituent, or fiber. Useful and nonlimiting examples of bioabsorbable or biodegradable polymeric materials may include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D(L-lactide-co-glycolide) (PLA/PGA), polyglycolide-co-trimethylene carbonate) (PGA/PTMC), polydioxanone (PDS), Polycaprolactone (PCL), polyhydroxybutyrate (PHBT), poly(phosphazene)poly(D,L-lactide-co-caprolactone) PLA/PCL), poly(glycolide-co-caprolactone) (PGA/PCL), polyphosphate ester), and the like. Further, the stent 24 may include materials made from or derived from natural sources, such as, but not limited to, collagen, elastin, glycosaminoglycan, fibronectin and laminin, keratin, alginate, combinations thereof, and the like.

The electrical cabling to carry power and signals may be contained within the sheaths 16, 34, 36 for the imaging device or illumination device. Further, support circuitry for the imaging devices may be contained within a central handle (not shown) at the proximal end of the delivery device. The circuitry may be powered from batteries or a main supply connection. Video signals may be routed out through the central handle for display or processing of the imagining information. Video signals may be transmitted remotely. The devices may include a power supply. The power is supplied to the camera and illumination system by various means such as hardwires or conductive material embedded into the sheath of which the camera is located to allow the current to run from the power source to the individual cameras/illumination device.

The imaging devices 12 may include but are not limited to cameras such as imaging chip and a lens, i.e. omnivision image chip with about 77 kpixels, CMOS or CCD in nature and a lens constructed with single or multiple optical elements. Additionally, the camera may acquire an image through an imaging fiber bundles rather than directly. The images from the cameras are sent as imaging signals through hardwires or other signal transmitting members or wirelessly transmitted for reception and processing for display on an external device. The cameras are of a size and shape driven by the mechanical attributes of the stent delivery system described. It is suggested that the camera is miniature in nature with resolution limited only by the state of the art of imaging arrays and lens construction, i.e., minimum imaging array pixel sizes continue to shrink and lenses such as, but not limited to, micro-lenses and wafer-scale lenses. The camera is positioned on the stent deployment device in such a way as to image specific areas of interest during navigation or stent deployment and therefore may have a primary direction of view at any angle. Camera lens parameters can be tuned at design to fulfill specific requirements of the application e.g., Field of View, Depth of View, Magnification. Additionally, the camera may include one or several imaging fiber bundles wherein fiber optics is used instead of a camera, i.e. similar to BSC Spyglass® Imaging System. The images from the camera may be sent as imaging signals through hardwires or other signal transmitting members including remote transmission to an external display device. Additionally, the camera can be a rotation camera such that it moves forward into the transparent tip 22, 38 or rotates about its imaging axis to different positions/angles within its socket. Further, camera may have any type of lenses depending on goal, i.e. fixed lenses, focusable lenses, wide angle, macro/micro lens, and the like.

The illumination device or system provides light for the operation within a body lumen. The illumination device may include, but is not limited to, a light emitting diode or a number of light emitting diodes, a fiber optic illumination guide for providing light from a light source, such as a laser or a white light source, and the like. Further a lens may also be provided at the distal end of illumination device to focus the illumination on the bodily lumen or tissue. The illumination device may include fibers and/or light-emitting diodes (LED). The light can be provided as a separate light source from the camera/camera processor or combined into a single piece of equipment. This equipment is located remotely from the stent deployment device and positioned as a matter of convenience to the practitioner. The light can also be produced by one or more LEDs located close to each camera. In this configuration, power is supplied to the LEDs via suitable electrical wires to provide simultaneous or independent control of LED light output. The illumination system may include a plurality of illumination devices such as optical fibers that terminate at different locations on the external surface of the inner member sheath or ends of the sheath. Further, the illumination system may include a single device in conjunction with the camera. The illumination device and/or camera may include, but is not limited to, an objective lens and fiber optic imaging light guide communicating with a practitioner, a camera, a video display, a cathode ray tube (CRT), a liquid crystal display (LCD), digital light processing (DLP) panel, a plasma display panel (PDP), a light-emitting diode (LLE) display, an organic light-emitting diode (OLED) display, a sensor, such as a charge-coupled device (CCD) sensor or a complementary metal oxide semiconductor (CMOS) sensor, and the like for use with a viewing device such as computer displays, video monitors, televisions, and the like. In any of the illumination configuration described, control of the light source or sources may be controlled manually or automatically through camera processor driven feedback control. Manual control of the illumination may be coupled with automatic control of the camera pixel gains or automatic control of the illumination may be coupled with automatic camera pixel gain control. Illumination may be provided through the far inner member or beneath the balloon as the balloon may be transparent.

Additionally, it is contemplated that mirrors or reflective surfaces may be added to the various embodiments to provide reflective viewing. For example, a mirror located distally may be positioned for the camera to view mirror images therethrough and vice versa. Further, mirrors may be moveable and adjustable to provide a range of viewing from the mirror.

In another aspect, a method for delivering a stent into a bodily lumen or a method of use is provided. The device 10, 30 may be used for various applications such as esophageal stenting, colonic stenting, pulmonary stenting, urinary stenting, for various applications for orifice transluminal endoscopic surgery (NOTES), biopsy procedures, and the like. The method of use includes providing a deployment device 10, 30. The device 10, 30 includes at least one sheath 16, 34 or stent retaining member to retain the prosthesis, such as a stent 24, in a compressed state until delivery, a dilation balloon 20, 40 and at least one imaging device 12 and/or illumination system 13 located on and attached to an inner member 18, 32. The at least one sheath 16, 34 has a proximal end, a distal end, an outer wall, and a longitudinal channel through the sheath defining an inner wall 28 of the sheath 16, 34 and the stent 24 is juxtaposingly disposed to a distal portion of the inner wall 28, and an inner member 16, 34 slidably disposed within the channel. The imaging device 12 is activated to provide imaging during the delivery of the stent and the illumination system 13 is activated to provide illumination within the lumen during the deployment process. The tip 29, 46 of the deployment device 10, 30 is advanced through the lumen to the stricture location until properly positioned. The dilation balloon 20, 40 is advanced through stricture. The dilation balloon 20, 40 is expanded within the stricture by inflating the balloon with fluid, such as saline, air, contrast or other fluids supplied by the inner member 18. The dilation balloon 20, 40 is inflated to push on the stricture, opening the lumen to a wider diameter at the stricture location. The dilation balloon 20, 40 is deflated and the deployment device 10, 30 is further advanced through the lumen to align the stent deployment portion of the deployment device 10, 30 to the desired location at the stricture point to release of the stent 24. Meanwhile, the imaging device 12 provides viewing of the advancement of the deployment device 10, 30; the inflation/deflation balloon 20, 40; further advancement of transparent tip 22, 52 through stricture; and deployment of stent 24. Once the deployment device 10, 30 is positioned for deployment, the stent 24 may be released from the endoscopic stent deployment device 10, 30 by retracting the elongate sheath to release the stent 24 from the deployment device 10, 30 and/or by advancing the sheath to push the stent 24 out of the deployment device 10, 30. The imaging device 13 provides imaging throughout the deployment of the stent 24 to verify accuracy and placement of the stent 24. The step of providing the deployment device 10, 30 may further include a step of loading the stent 24 within the inner wall of the sheath 16, 34 prior to use within the body of a patient. The method may further include radially compressing the stent 24 prior to loading the stent 24 within the sheath 16, 34.

Additionally, the method of use includes selecting the proper prosthesis according to the patient anatomy and disease progression; loading the desired prosthesis into the deployment device 10, 30 or selecting a pre-loaded deployment device 10, 30 including the proper prosthesis; connecting the deployment device to external capital equipment to supply power and necessary external elements to the device; introducing the device through the desired orifice and extending the device through a lumen to the location of die stricture for deployment; confirming proper positioning by direct visual confirmation and exploring the lumen and/or stricture to ensure proper placement of prosthesis, i.e., the esophago-gastroenoscopy (EGD) is performed by the device; measuring the stricture and recording the measurements; advancing the dilation balloon through the stricture; inflating the dilation balloon to open the stricture; deflating the dilation balloon; deploying the prosthesis by pulling back on the sheath while the physician watched the deployment under direct visualization by the cameras; ensuring proper placement of the prosthesis by direct visualization once the prosthesis has been deployed; removing the device from the lumen. Additionally, the imaging device and/or illumination system may be attached to the device prior to introducing the device with the lumen.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. A prosthesis deployment system comprising:
    a first outer sheath including a distal end including a distal end face of the first outer sheath, a proximal end, an outer circumferential surface and a channel extending between the distal end of the first outer sheath and the proximal end of the first outer sheath;
    an inner tubular member slidably extending through the channel of the first outer sheath;
    a prosthesis extending in a compressed state within the channel and surrounding the inner tubular member;
    a dilation balloon fixed to the inner tubular member and in fluid communication with a lumen of the inner tubular member for inflation of the dilation balloon, the dilation balloon positioned distal to the first outer sheath;
    a transparent tip fixed to the inner tubular member, the transparent tip positioned between the distal end of the first outer sheath and the dilation balloon, wherein a proximal end face of the transparent tip abuts the distal end face of the first outer sheath, wherein the transparent tip is solid;
    an imaging device located at the distal end of the first outer sheath,
    wherein the transparent tip includes a cylindrical portion abutting the distal end of the first outer sheath.

2. The prosthesis deployment system of claim 1, wherein the imaging device is flush with the distal end face.

3. The prosthesis deployment system of claim 1, wherein the outer circumferential surface of the first outer sheath extends between the distal end and the proximal end of the first outer sheath, wherein the transparent tip contacts the outer circumferential surface of the first outer sheath.

4. The prosthesis deployment system of claim 1, wherein the imaging device is located in a lumen extending through the first outer sheath, the imaging device being moveable within the lumen.

5. The prosthesis deployment system of claim 1, wherein the transparent tip includes a conical portion.

6. The prosthesis deployment system of claim 5, wherein the cylindrical portion is located proximal of the conical portion.

7. The prosthesis deployment system of claim 6, wherein the cylindrical portion extends from the distal end of the first outer sheath and has a similar outside circumference as the first outer sheath, and the conical portion extends from the cylindrical portion towards the dilation balloon, a diameter of the conical portion reduces in size in a distal direction.

8. The prosthesis deployment system of claim 1, further comprising a second outer sheath, wherein the first outer sheath is independently slidable within the second outer sheath.

9. The prosthesis deployment system of claim 8, wherein the imaging device is attached to the second outer sheath.

10. The prosthesis deployment system of claim 9, wherein the prosthesis is juxtaposingly disposed to an inner wall of the first outer sheath.

11. The prosthesis deployment system of claim 1, wherein the transparent tip has a proximal end at the proximal end face, and a distal end, the distal end of the transparent tip having a smaller diameter than a diameter of the transparent tip at the proximal end of the transparent tip.

12. The prosthesis deployment system of claim 11, wherein the distal end of the transparent tip abuts the dilation balloon.

13. The prosthesis deployment system of claim 12, wherein the first outer sheath is independently movable relative to the inner tubular member.

14. The prosthesis deployment system of claim 1, wherein the imaging device protrudes from the distal end face of the first outer sheath and extends into a void in the transparent tip.

15. The prosthesis deployment system of claim 1, wherein the inner tubular member is a single tubular element, wherein distal and proximal ends of the dilation balloon are both attached to the single inner tubular member.

16. A stent deployment system comprising:
    an inner sheath, the inner sheath including a distal end including a distal end face of the inner sheath, a proximal end, an outer circumferential surface and an inner wall defining a lumen extending therethrough;
    an outer sheath extending around the inner sheath, the outer sheath being independently movable relative to the inner sheath, the outer sheath including a distal end face;
    an inner tubular member slidably extending through the lumen of the inner sheath, the inner tubular member having a distal tip at a distal end thereof;
    an imaging device positioned at the distal end face of the outer sheath or at the distal end face of the inner sheath;
    a dilation balloon fixed to the inner tubular member proximal of the distal tip of the inner tubular member; and
    a transparent tip fixed to the inner tubular member, the transparent tip positioned between the distal end face of the inner sheath and the dilation balloon; wherein a proximal end face of the transparent tip abuts the distal end face of the inner sheath, wherein the transparent tip is solid.

17. The stent deployment system of claim 16, wherein the imaging device protrudes from the distal end face of the inner sheath and extends into a void in the transparent tip.

18. The stent deployment system of claim 16, wherein the imaging device is located in a second lumen extending through the inner sheath, the imaging device being moveable within the second lumen.

19. The stent deployment system of claim 16, wherein a proximal end of the transparent tip has a similar outside circumference as the distal end of the inner sheath.

20. The stent deployment system of claim 16, wherein a distal end of the transparent tip abuts the dilation balloon.

\* \* \* \* \*